United States Patent [19]
Holland

[11] Patent Number: 5,838,419
[45] Date of Patent: Nov. 17, 1998

[54] METHOD AND APPARATUS FOR TREATING REFRACTIVE EYE ABNORMALITIES

[76] Inventor: Stephen Holland, 1108 W. Nassau Dr., Peoria, Ill. 61615-1379

[21] Appl. No.: 605,377

[22] Filed: Feb. 22, 1996

[51] Int. Cl.$^6$ .............................. G02C 7/02; G02C 7/04; G02C 7/10; A61F 2/16
[52] U.S. Cl. ........................ 351/177; 351/162; 351/163; 351/165; 351/176; 623/6
[58] Field of Search .......................... 351/160 R, 160 H, 351/161, 162, 177, 163, 165, 176; 623/6

[56] References Cited

U.S. PATENT DOCUMENTS

| | | |
|---|---|---|
| 1,856,163 | 5/1932 | Jones . |
| 3,963,330 | 6/1976 | Boniuk ................................. 351/163 |
| 3,996,627 | 12/1976 | Deeg et al. ................................. 3/13 |
| 4,542,964 | 9/1985 | Gilson et al. ............................ 351/44 |
| 4,655,565 | 4/1987 | Freeman ............................. 351/160 R |
| 4,795,462 | 1/1989 | Grendahl ..................................... 623/6 |
| 4,952,046 | 8/1990 | Stephens et al. ....................... 351/163 |
| 5,044,743 | 9/1991 | Ting ....................................... 351/163 |
| 5,187,207 | 2/1993 | Gallas .................................... 523/106 |
| 5,218,386 | 6/1993 | Levien ................................... 351/163 |
| 5,235,358 | 8/1993 | Mutzhas et al. ........................ 351/163 |
| 5,243,460 | 9/1993 | Kornberg ................................. 359/464 |
| 5,305,027 | 4/1994 | Patterson .................................. 351/44 |
| 5,400,175 | 3/1995 | Johansen et al. ....................... 359/361 |
| 5,408,278 | 4/1995 | Christman ................................. 351/44 |

OTHER PUBLICATIONS

"Color Temperature: Light Source Conversion With Filters", *Kodak Photographic Filters Handbook*, ISBN 0-87985-658-0, pp. 46-53.

M. Born and E. Wolf, "Chapter VI: Image–Forming Instruments", *Principals of Optics*, 6th Edition, Pergamon Press, Elmsford, New York, pp. 233-235, 1980.

Millodot, Michel and Ronald W. Stevenson, "Electrophysiological Evidence of Adaptation to Colored Filters", *American Journal of Optometry & Physiological Optics*, vol. 59, No. 6, pp. 507-510, 1982.

Elio Raviola, M.D. and Torsten N. Wiesel, M.D., "Special Article: An Animal Model of Myopia", *The New England Journal of Medicine*, vol. 312. No. 25, pp. 1609-1615, Jun., 20, 1985.

Gonzalez, Rafael C., *Digital Image Processing*, Addison–Wesley Publishing Company, Plates II and IV, Nov., 1987.

Phillips, Calbert I., "Aetiology of myopia", *British Journal of Opthamology*, vol. 74, pp. 47-48, 1990.

Lide, David R., Ed., *CRC Handbook of Chemistry and Physics*, CRC Press, pp. 10-291-10-305, 1991-1992 edition.

Ronald W. Waynant and Marwood N. Ediger, "Chapter 2: Noncoherent Sources", *Electro–Optics Handbook*, p. 2.1, 1994.

Norton, Thomas T., PhD, "A New Focus on Myopia", *JAMA*, vol. 271, No. 17, pp. 1362-1363, May, 4, 1994.

*Primary Examiner*—Scott J. Sugarman
*Attorney, Agent, or Firm*—Sterne, Kessler, Goldstein & Fox P.L.L.C.

[57] ABSTRACT

A method for treating refractive eye abnormalities, including myopia, hyperopia, and astigmatism, by shifting the spectral distribution of incident light is described. Optical filters or tints are provided on eyeglasses, contact lenses, intra-ocular implants, or at ambient light sources to shift the spectral distribution of light entering the eye being treated. Ambient light sources emitting at specified spectral distribution or wavelength range can also be used. In this way, the average spectral distribution of visible light incident to an eye is controlled to treat refractive eye abnormalities. Changes in the eyeball shape and focus resulting from an eye's response to the spectral distribution of light are prevented, mitigated, halted, or even reversed. The visible spectral content is shifted to shorter or longer wavelengths over an entire field of view detected by the retina to treat myopia and hyperopia respectively. To correct for astigmatism, the spectral distribution of light is shifted within selected areas of a retina field of view corresponding to an abnormal power.

42 Claims, 1 Drawing Sheet

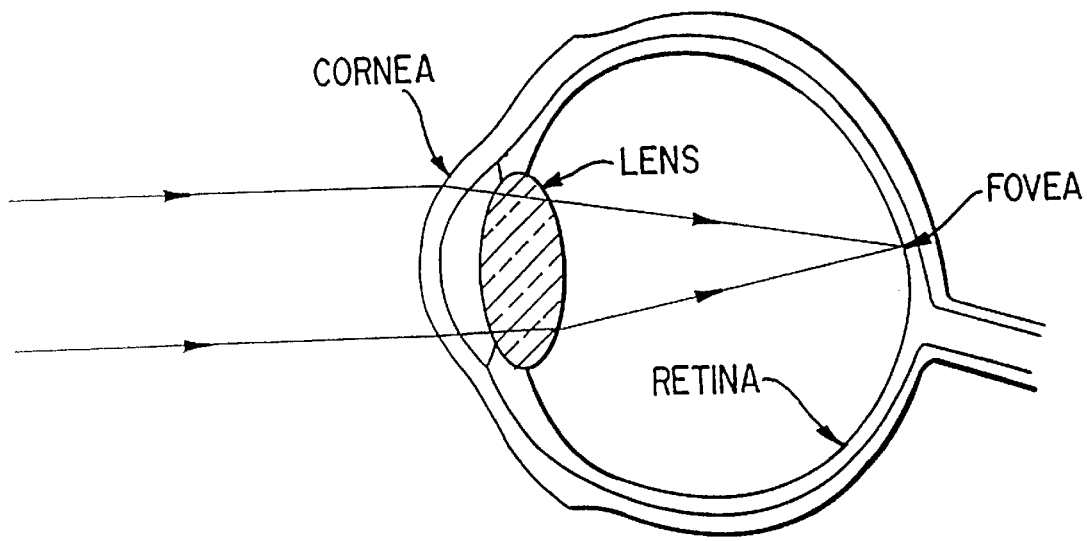

METHOD AND APPARATUS FOR TREATING REFRACTIVE EYE ABNORMALITIES

BACKGROUND OF THE INVENTION

1. Field of the Invention

The present invention relates to the treatment of refractive eye abnormalities. More particularly, the present invention relates to treatments for myopic, hyperopic, and astigmatic eye conditions.

2. Related Art

The Figure shows the focusing of distant object light in an eye. A cornea on the outer surface of the eye and an interior lens focus an incident image at a focus position F along the optical axis of the eye. The retina is composed of two types of light sensitive cells called rods and cones which detect the image and provide a neurological response to the brain. The image appears in-focus when the focus position F is located at the retina. See, e.g. Born, M. and Wolf, E., *Principles of Optics*, 6th Ed., Pergamon Press: Elmsford, N.Y., pp. 233–235, 1980 (incorporated by reference herein).

Refraction mostly occurs at the cornea on the outer surface of the eye and at the two surfaces of the lens in the eye. Thus, the focus position of an image depends on the eyeball shape and the curvature of the cornea and lens. Muscular contractions alter the radius of curvature of the interior lens to maintain a focus at the retina as the eye observes different scenes. The adjustment of the eye for focusing is known as accommodation.

The spectral content of an image also affects the focus position F. In general, the refraction of any convex lens, including the eye, depends upon the wavelength of the light passing through the lens. Different optical wavelengths or colors are focused within the eye to different locations relative to the retina. Due to this chromatic aberration, short visible wavelengths such as blue light come to a focus at a focus position slightly forward of long visible wavelengths such as red light.

Three basic types of refractive eye abnormalities can occur: myopia, hyperopia, and astigmatism. Myopia or nearsightedness results when infinite rays are focused anterior to the retina. Hyperopia or farsightedness refers to the complementary condition where infinite rays are brought to focus behind the retina. Astigmatism refers to the condition where the power of the eye varies over the retina field of view. Thus, in an astigmatic eye, different regions of the field of view can have different focus positions in front of (anterior to), on, or behind (posterior to) the retina.

Refractive errors in the eye are common. Nearsightedness alone affects 25% of Americans. In some regions of the world, 75% of people have myopia. Hyperopia and astigmatism also limit the vision of millions of people worldwide. Thus, treatments which cure or ameliorate eye refractive abnormalities have a widespread benefit.

At present, corrective refractive lenses, i.e., eyeglasses or contact lenses, are prescribed to correct vision but do not consider the accommodation or response of the eye to ambient light. Emerging surgical techniques such as laser etching are expensive. Without regard to eye refractive abnormalities, filters are used to shift the spectral distribution of light incident upon an eye. Protective lenses often use blocking filters to block ultraviolet radiation or blue light. Other filters decrease glare, enhance color perception, or achieve a cosmetic result.

What is needed is a simple method for treatment of refractive eye abnormalities having widespread application.

Further, the inventor has found that a treatment for refractive eye abnormalities is needed which considers the response of an eye to the spectral distribution of ambient light.

SUMMARY OF THE INVENTION

The present invention provides a treatment for refractive eye abnormalities, including myopia, hyperopia, and astigmatism, by shifting the spectral distribution of incident light. Optical filters or tints are provided on eyeglasses, contact lenses, intra-ocular implants, or at ambient light sources to shift the spectral distribution of light entering the eye being treated. Ambient light sources emitting at specified spectral distributions can also be used. In this way, the average spectral distribution of visible light incident to an eye is controlled to treat refractive eye abnormalities.

To treat a patient, filters are used to modify the spectral content of light entering the eye. For example, relatively long or short visible wavelengths, including red or blue light, are identified as potentially causing myopic, hyperopic, and astigmatic refractive eye abnormalities to develop or worsen. Blue filters are used to treat myopia, red filters are used to treat hyperopia, and combinations of filters are used to treat astigmatism..

Myopia is treated by shifting the spectral distribution towards short visible wavelengths. Optical filters or other optical mechanisms having a dominant transmittance at or near short visible wavelengths in the range of 380 to 590 nanometers (nm.), and in particular a range including blue light 430 to 530 nm., are used to treat myopia according to the present invention. For patients exposed to modern artificial lights having a reddish spectral content compared to natural light, a light conversion filter is used to render cooler balanced daylight color under tungsten illumination. One or more Wratten 80 series photographic filters, i.e. two Wratten 80C filters (dominant wavelength approximately 470 nm.), can be used in this myopia treatment.

Hyperopia is similarly treated by shifting the spectral distribution towards long visible wavelengths. Optical filters or other optical mechanisms having a relatively great transmittance at or near long visible wavelengths in the range of 590 to 800 nm., and in particular a range including red light 600 to 700 nm., are used to treat hyperopia according to the present invention.

Astigmatism is treated using a combination of the methods used to treat myopia and hyperopia. The spectral distribution of light within selected areas of a retina field of view having an abnormal power are shifted to correct for astigmatism. In one example, an optical filter element has blue filters and/or red filters in different sections, such as quadrants. A blue filter section is used to correct an astigmatic refractive eye error which focuses light in front of a retina section. A red filter section is used to correct an astigmatic refractive eye error which focuses light behind a retina section.

Further features and advantages of the present invention, as well as the structure and operation of various embodiments of the present invention, are described in detail below with reference to the accompanying drawing.

BRIEF DESCRIPTION OF THE DRAWING

The accompanying drawing, which is incorporated herein and form part of the specification, illustrates the present invention and, together with the description, further serves to explain the principles of the invention and to enable a person skilled in the pertinent art make and use the invention.

The figure is a diagram of a human eye.

The present invention will now be described with reference to the accompanying drawing.

DETAILED DESCRIPTION OF THE PREFERRED EMBODIMENTS

Table of Contents

I. Definitions and Overview
II. Discovery of Ambient Light as a Source of Refractive Eye Error
III. Treatment of Myopia
IV. Treatment of Hyperopia
V. Treatment of Astigmatism
VI. Conclusion

I. Definitions and Overview

The terms "treat" and "treatment" of refractive eye are used throughout the specification with reference to the present invention to mean a treatment for refractive eye abnormalities which can prevent or slow development of a refractive eye abnormality prior to diagnosis and which can slow, halt, or reverse progression of an existing refractive eye abnormality condition.

"Visible light" is used broadly herein to refer to that region of the electromagnetic spectrum (380 to 800 nanometers) to which the human eye can naturally detect or respond. See, e.g., the broadest cut-offs for a visible region between ultraviolet and infra-red regions as described by Waynant et al. Eds. in *Electro-Optics Handbook* (McGraw Hill, Inc.: New York 1994), page 2.1 (incorporated by reference herein). See, also, the spectrum of visible colors shown generally in a chromaticity diagram shown by Gonzalez, Ed., in *Digital Image Processing*, 2nd Ed. (Addison-Wesley Publishing Co.: Reading, Mass. 1987), Plates II and IV (incorporated by reference herein).

The terms "blue" and "red" as used with reference to the present invention refer to the two ranges of visible wavelengths which can be used to treat myopia, hyperopia, and astigmatism respectively as described below. For instance, blue light refers to relatively short visible wavelengths, including but not limited to, blue and blue-green colors, also called "cool" colors. Red light refers to relatively long visible wavelengths, including but not limited to, red, orange, amber, and yellow colors.

The present invention is described with respect to a clinical treatment for preventing, halting or curing refractive eye abnormalities in people. The methods for treatment have universal application to all people including children, adults, men, and women. Alternative environments and applications will become apparent to one skilled in the art given this description and are included in the scope of the present invention.

The present invention provides a treatment for refractive eye abnormalities, including myopia, hyperopia, and astigmatism, by shifting the spectral distribution of incident light. Optical filters or tints are provided on eyeglasses, contact lenses, intra-ocular implants, or at ambient light sources to shift the spectral distribution of light entering the eye being treated. Ambient light sources emitting at a specified spectral distribution can also be used. In this way, the average spectral distribution of visible light incident to an eye is controlled to treat refractive eye abnormalities. Changes in the eyeball shape and focus resulting from an eye's response to the spectral distribution of light are prevented, mitigated, halted, or even reversed.

The visible spectral content is shifted to shorter or longer wavelengths over an entire field of view detected by the retina to treat myopia and hyperopia respectively. To correct for astigmatism, the spectral distribution of light is shifted within selected areas of a retina field of view corresponding to an abnormal power.

II. Discovery of Ambient Light as a Source of Refractive Eye Error

As described earlier, accommodation is the adaption of the eye, and in particular the interior lens, which permits the retinal focus of images at different distances. The accommodation response is further influenced by the spectral content of incident light. When exposed to red light, the eye naturally accommodates with a response that focuses light behind the retina. Such accommodation involves changing the surface curvatures of the interior lens to move the focus behind the retina. Myopia results when the eye elongates longitudinally so that the retina is too far posterior to allow correct focusing. An elongated eyeball is characteristic of nearsightedness.

Animal models of myopia further show a variety of ways that an eyeball tends to elongate including the presence of ambient red light. Lid fusion causes myopia in susceptible animals. This is equivalent to diffuse illumination of the retina with red light. The lengthening process does not happen when the animals are raised in the dark. See, Raviola, E. and Wiesel, T., "An Animal Model of Myopia," *New England Journal of Medicine*, 312: 1609–1615 (1985) (incorporated by reference herein). Similar results are reported in a brief survey of animal models by Philips, "Aetiology of Myopia," *British Journal of Ophthalmology* 74:47–48 (1990) (incorporated by reference herein).

Modern living in industrial societies entails a great deal of exposure to artificial light. Artificial light such as incandescent light has much more spectral content in the red end of the visible spectrum compared to natural sunlight. In this regard, it is interesting to note that there is an association between the development of myopia and doing work with objects near to the eye or "near work." While studies have looked at near work as a cause of myopia, perhaps it is the incandescent illumination that is the real culprit. Further, a related historical observation can be made that early paintings of people with glasses show monks in monasteries with manuscripts illuminated by candles rich in red spectral components.

Red-biased light from artificial sources causes images to be focused further back in the eye than images formed under natural lighting. In response, the retina induces the eye to elongate. The interior lens adjusts and can send the image even further back. The retina then chases an image which is not well-focused. Chromatic aberration and incomplete compensation by the eye, therefore, exacerbates the problem as longer red colors are brought to a focus behind shorter blue colors. Indeed the above-referenced animal experiments further corroborate that the eye elongates as a response to light that is not well focused (the diffusion experiments) and to light that is red (the closed lid animal models).

Thus, the inventor has discovered that modern artificial light sources with a higher red spectral content than natural sunlight are likely associated with the development of a myopic eye condition. In particular, when the eye is exposed to ambient light having a high red spectral content, the eye is driven to elongate along its axial length. Moreover, selective diffusion experiments suggest that when only selected areas of a retinal field of view are not well-focused, only those corresponding exposed parts of the eyeball globe, i.e. the corresponding exposed retina sections, become elongated.

Similar converse responses are likely by the eye when exposed to ambient blue light which is comes to a focus too far forward in the eye. The natural accommodation of the eye can further focus the blue light too far forward and drive the eye to shorten along its axial length, or fail to elongate sufficiently during growth and development, creating a hyperopic refractive eye error over time.

III. Treatment of Myopia

In a first embodiment, myopia or nearsightedness is treated by shifting the spectral distribution of incident light towards shorter visible wavelengths. In one example, optical filters or tinting having a relatively high transmittance in a short wavelength range of the visible spectrum between 380 to 590 nm. are provided in front of the eye or at ambient light sources. Even more specifically, blue filters or tinting having a maximum transmittance percentage for light in a wavelength range which includes blue light, i.e. 430 to 530 nm. are used. See, e.g., visible transmissive, blue and blue-green colored filters manufactured by Corning and Kodak as listed by Lide, D. Ed., *CRC Handbook of Chemistry and Physics*, 72nd. Edition, (CRC Press: Boca Raton 1991), pp 10-291 to 10-305 (incorporated by reference herein).

Another example of the present invention treats myopia using specific light conversion filter(s) which shift the spectral content of reddish artificial ambient light closer to natural sunlight. For instance, any of the blue light balancing 80-series Wratten filters (80A to 80D) manufactured by Kodak can be used. See, e.g., the *CRC Handbook* referenced above page 10-299.

Preferably, a filter or filter combination equivalent to two 80C filters is used as described below. These light conversion filters are used in photographic film exposure under tungsten illumination to render cooler colors balanced for daylight film. In this way, the average spectral distribution of incident light is shifted to approximate more closely natural sunlight, thereby, avoiding or reversing the discovered adverse effects of reddish artificial light which causes an eye to elongate.

Incandescent illumination can be modeled as a blackbody radiator and characterized by the color temperature of the light distribution. Daylight characteristically has a color temperature of 5400° Kelvin (K). A typical 100 Watt light bulb has a color temperature of 2900° K. Color filters can be characterized by the apparent shift in color temperature they induce using a Mired shift value $\Delta M/K$. Thus, the light source color conversion performed by one or more filters can be characterized by a Mired shift value $\Delta M/K$:

$$\Delta M/K = 1{,}000{,}000 \ (1/T_1 - 1/T_2), \text{ tm} \quad (1)$$

where $T_1$ is the color temperature of the original source and $T_2$ is the color temperature of the light through the one or more filters. See, e.g., *Kodak Photographic Filters Handbook* (ISBN 0-87985-658-0) pages 46 to 53 (incorporated herein by reference).

Color conversion from a 2900° K to 5400° K light source to treat myopia according to this example embodiment requires a Mired shift value:

$$\Delta M/K = 1{,}000{,}000 \ (1/5400 - 1/2900) = 185 - 345 = -160. \quad (2)$$

Myopia is then treated using one or more filters having a combined Mired shift value of approximately −160. Two Wratten 80C filters manufactured by Kodak, each having a Mired shift value of −81, can be used for myopia treatment according to the present invention.

More generally, a variety of optical devices can be used to blue-shift the spectral content of incident light to treat myopia depending upon a particular clinical need or application. Eyeglasses, contact lenses, and/or intraocular implants having blue tint or blue filters are prescribed for correcting or preventing myopia. For example, a patient with myopia wears prescribed eyeglasses coated with blue tinting duplicating the Wratten 80 family filter characteristics (dominant wavelength at or near 470 nm.), regardless of any other corrective prescription, until the eyes correct fully or until a new prescription is needed. For patients exposed to incandescent illumination, blue-tinted or blue-filtered eyeglasses and contact lenses are prescribed—even for emmetropic eyes to prevent development of myopia.

In situations requiring prolonged close scrutiny, blue-tinting or blue filters are applied to light sources and fixtures to prevent eye strain and to prevent or reverse development of myopia. For example, nearsightedness and its worsening due to near work are corrected by applying blue-tint or blue filters to magnifying lenses used in inspection, computer or CRT displays, and ambient light sources. Emission characteristics of display screen phosphors or color balance are adjusted to have a higher blue spectral content to prevent or reverse development of myopia.

Work light or home light preferably includes light sources having a spectral distribution close to that of sunlight. For example, halogen lights have a spectral distribution closer to natural sunlight than tungsten light bulbs. Fluorescent light bulbs with phosphors selected to produce more blue light and less red light also more closely approximate sunlight than cool white fluorescent bulbs. Any of these relatively blue light sources can be used as an adjunct to blue-filtering or alone to prevent or reverse development of myopia.

An optional method for treating myopia is to under correct a patient's vision by 0.01 to 5.00 diopters to bring the image forward of the retina while adjusting the spectral balance towards short visible wavelengths, i.e. blue. The natural chromatic aberration of the eye lens in focusing blue light more forward can obviate the need for an under-correction maneuver.

Finally, all of these treatment methods are unique in that they take advantage of the previously unrecognized and unsuspected role that modern reddish lights play in the development of myopia.

IV. Treatment of Hyperopia

Similar principles are used in the present invention to treat other refractive eye errors. In a second embodiment of the present invention, hyperopia (farsightedness) is treated by shifting the spectral distribution of the light entering the eye towards long visible wavelengths. In one example, optical filters or tinting having a high transmittance in a long wavelength range of the visible spectrum between 590 to 800 nm. are provided in front of the eye or at ambient light sources. Even more specifically, reddish filters or tinting having a maximum transmittance percentage for light in a wavelength range which includes red light, i.e. 600 to 700 nm. are used. See, e.g., visible transmissive, red, orange, amber, and yellow colored filters manufactured by Corning and Kodak as listed in the *CRC Handbook* previously incorporated by reference on pages 10-291 to 10-305. In this way, the average spectral distribution of incident light is red-shifted.

As with the myopia treatments, a variety of devices can be used to red-shift the spectral content of incident light to treat hyperopia depending upon a particular clinical need or application. Eyeglasses, contact lenses, or intraocular implants having red tint or red filters are prescribed for correcting or preventing myopia. For example, a patient with hyperopia wears red-tinted eyeglasses and/or contact lenses until the eyes correct fully or until a new prescription is needed. For patients exposed to blue illumination or for whom hyperopia is expected for reasons of hereditary or other factors, red-tinted eyeglasses are prescribed—even for emmetropic eyes to prevent development of hyperopia.

Where hyperopia is a concern, work light or home light preferably includes light sources having a high red spectral content such as tungsten light bulbs or fluorescent light bulbs with phosphors selected to produce more red light and less blue light. Any of these red-shift light sources can be used as an adjunct to red-filtering or alone to prevent or reverse development of hyperopia. Red-tint and/or red-filters can also be applied to computer or cathode ray tube (CRT) displays and magnifying inspection lens. Red display screen phosphors or reddish television/CRT color balance can be used to further improve the shifting of incident light. Where ambient light in a room or larger areas is spectrally-shifted toward longer wavelengths to treat hyperopia, consideration should be made regarding the impact upon people with myopic or emmetropic eyes (and vise versa).

An optional method for treating hyperopia is to under-correct a patient's vision by 0.01 to 5.00 diopters to bring the image behind the retina while adjusting the spectral balance towards long visible wavelengths, i.e. red. The natural chromatic aberration of the eye lens focusing red light rearward can obviate the need for an under-correction maneuver.

V. Treatment of Astigmatism

Finally, in a third embodiment astigmatism is treated using a combination of the methods used to treat myopia and hyperopia as described above. The spectral distribution of light within selected areas of a retina field of view having an abnormal power are shifted to correct for astigmatism.

In one example, an optical filter element has blue and/or red filters in different sections, i.e. quadrants. A blue filter section is used to correct an astigmatic refractive eye error which focuses light in front of a corresponding retina section. A red filter section is used to correct an astigmatic refractive eye error which focuses light behind a corresponding retina section. The blue filter section can have a relatively high bluish transmissivity as described above with respect to myopia treatment. The red filter section can have a relatively high reddish transmissivity as described above with respect to hyperopia treatment. In this way, the localized response of the eye acts to move each retina section forward or backward in response to illumination of the selected retina sections by the filtered incident light so as to prevent or reverse development of astigmatism.

VI. Conclusion

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for treating a refractive abnormality, comprising the steps of:
    identifying a refractive abnormality of an eye; and
    treating said refractive abnormality by controlling a spectral power distribution of visible light incident to the eye to effect a change in the shape of the eve over time.

2. The method of claim 1, wherein said refractive abnormality comprises at least one refractive abnormality selected from the group of myopia, hyperopia, and astigmatism.

3. The method of claim 1, wherein said spectral power distribution controlling step comprises the step of filtering incident light to the eye.

4. The method of claim 3, wherein said filtering step comprises the step of providing at least one blue light filter in a field of view of the eye to treat myopia.

5. The method of claim 4, wherein said providing step comprises the step of converting the spectral power distribution of ambient artificial light to approximate the spectral distribution of sunlight.

6. The method of claim 4, wherein said at least one blue light filter has a Mired shift value approximately equal to −160; and said providing step comprises the step of converting the spectral power distribution of ambient light using said at least one blue light filter having a Mired shift value approximately equal to −160.

7. The method of claim 6, wherein said at least one blue light filter comprises two Wratten 80C filters; and said providing step comprises the step of converting the spectral power distribution of ambient light using the two Wratten 80C filters.

8. The method of claim 3, wherein said filtering step comprises the step of providing at least one red filter to treat hyperopia.

9. The method of claim 3, wherein said filtering step comprises the step of providing a sectioned-filter having at least one of red and blue sections to treat astigmatism.

10. The method of claim 1, wherein said spectral power distribution controlling step comprises filtering ambient light sources.

11. The method of claim 1, wherein said spectral power distribution controlling step comprises providing at least one ambient light source to provide a spectral power distribution of ambient visible light to treat the refractive abnormality.

12. The method of claim 11, wherein said refractive abnormality comprises myopia, and wherein said providing step comprises operating a blue ambient light source means which emits blue light to provide near work illumination.

13. The method of claim 4, further comprising the step of undercorrecting vision to bring an image formed by the visible light incident to the eye forward of the retina in the eye.

14. The method of claim 8, further comprising the step of undercorrecting vision to bring an image formed by the visible light incident to the eye behind the retina in the eye.

15. The method of claim 1, wherein said identifying step comprises the step of identifying myopia and astigmatism; and wherein said spectral power distribution controlling step comprises the steps of:
    filtering incident light to the eye to effect a change in the shape of the eye over time to treat the myopia; and
    filtering further the incident light in a portion of the field of view of the eye to effect a change in the shape of the eye over time to treat the astigmatism.

16. The method of claim 1, wherein said identifying step comprises the step of identifying hyperopia and astigmatism; and wherein said spectral power distribution controlling step comprises the steps of:

filtering incident light to the eye to effect a change in the shape of the eye over time to treat the hyperopia; and filtering further the incident light to the eye in a portion of the field of view of the eye to effect a change in the shape of the eye over time to treat the astigmatism.

17. An apparatus for treating myopia in an eye comprising:

an optical device for passing light to the eye; and a blue filter for filtering light passing through said optical device to the eye to effect a change in the shape of the eye over time to treat the myopia.

18. The apparatus of claim 17, wherein said optical device comprises at least one optical device selected from a group of eyeglasses, contact lenses, intra-ocular implants, and a magnifying lens.

19. The apparatus of claim 17, wherein said blue filter further comprises at least one of a blue tint and a blue optical filter.

20. The apparatus of claim 17, wherein said blue filter has a maximum transmittance percentage for light in a short wavelength range of the visible spectrum between 380 to 590 nm.

21. The apparatus of claim 17, wherein said blue filter has a maximum transmittance percentage for light in a short wavelength range of the visible spectrum between 430 to 530 nm.

22. The apparatus of claim 17, wherein said blue filter comprises light conversion means for converting the spectral power distribution of ambient artificial light to approximate the spectral power distribution of sunlight.

23. The apparatus of claim 17, wherein said blue filter comprises at least one light conversion filter having a Mired shift value approximately equal to −160 to treat myopia.

24. The apparatus of claim 23, wherein said at least one light conversion filter consists of two Wratten 80C filters.

25. A method for treating myopia in an eye, comprising the step of:

wearing the apparatus of claim 17 to effect a change in the shape of the eye over time to treat the myopia.

26. A light source apparatus for treating myopia, comprising:

a light source for emitting visible light; and a blue filter for filtering the emitted light incident to an eye to effect a change in the shape of the eve over time to treat the myopia.

27. An apparatus for treating hyperopia comprising:

an optical device for passing light to an eye; and a red filter for filtering light passing through said optical device to the eye to substantially block wavelengths less than 590 nm, and to effect a change in the shape of the eve over time to treat the hyperopia.

28. The apparatus of claim 27, wherein said optical device comprises at least one optical device selected from a group of eyeglasses, contact lenses, and intra-ocular implants.

29. The apparatus of claim 27, wherein said red filter further comprises at least one of a red tint and a red optical filter.

30. The apparatus of claim 27, wherein said red filter has a maximum transmittance percentage for light in a long wavelength range of the visible spectrum between 590 to 800 nm.

31. The apparatus of claim 27, wherein said red filter has a maximum transmittance percentage for light in a long wavelength range of the visible spectrum between 600 to 700 nm.

32. A method for treating hyperopia in an eye, comprising the step of:

wearing the apparatus of claim 27 to effect a change in the shape of the eye over time to treat the hyperopia.

33. A light source apparatus for treating hyperopia, comprising:

a light source for emitting visible light; and a red filter for filtering the emitted light incident to an eye to substantially block wavelengths less than 590 nm, and to effect a change in the shape of the eye over time to treat the hyperopia.

34. An apparatus for treating astigmatism comprising:

an optical device for passing light to an eye; and a sectioned-filter including red and blue filter sections for filtering light passing through said optical device to the eye to effect a change in the shape of the eve over time to treat the astigmatism.

35. The apparatus of claim 34, wherein said optical device comprises at least one optical device selected from a group of eyeglasses, contact lenses, and intraocular implants.

36. The apparatus of claim 34, wherein said sectioned-filter comprises at least one of a red filter section and a blue filter section, each red filter section includes at least one of a red tint and a red filter, and each blue filter section includes at least one of a blue tint and a blue filter.

37. A method for treating astigmatism in an eye, comprising the step of:

wearing the apparatus of claim 34 to effect a change in the shape of the eye over time to treat the astigmatism.

38. A method for treating myopia, comprising:

receiving incident visible light having a spectral distribution including red and blue spectral components at an eye; and filtering said spectral distribution of the received incident light passing to the eye to reduce the magnitude of red spectral components relative to the magnitude of blue spectral components to treat the myopia such that a response of the eye to red spectral components which causes the eye to lengthen is prevented, mitigated, or reversed.

39. A method for treating hyperopia, comprising the steps of:

receiving incident visible light having a spectral distribution including red and blue spectral components; and filtering said spectral distribution of the received incident light to reduce the magnitude of blue spectral components relative to the magnitude of red spectral components to treat the hyperopia such that a response of the eye to blue spectral components which causes the eye to shorten is prevented, mitigated, or reversed.

40. A method for treating astigmatism in an eye having at least first and second retina regions, wherein the astigmatism focuses light passing within the eye at a focus position behind the retina in the first retina region and in front of the retina in the second retina region, comprising the steps of:

receiving incident visible light having a spectral distribution including red and blue spectral components;

filtering a spectral distribution of the incident light in the field of view of the first retina region to reduce the magnitude of blue spectral components relative to the magnitude of red spectral components; and filtering a spectral distribution of the incident light in the field of view of the second retina region to reduce the magnitude of red spectral components relative to the magnitude of blue spectral components such that a response of the eye at the first retina section to blue spectral components which causes the eye to shorten is prevented, mitigated, or reversed, and a response of the eye at the second retina section to red spectral components which causes the eye to lengthen is prevented, mitigated, or reversed.

41. A method for treating astigmatism, comprising the steps of:

receiving incident visible light having a spectral distribution including red and blue spectral components; and filtering said spectral distribution of the received incident light to reduce the magnitude of red spectral components relative to the magnitude of blue spectral components to effect a change in the shape of the eye over time to treat the astigmatism in at least a portion of the field of view of an eye.

42. A method for treating astigmatism, comprising the steps of:

receiving incident visible light having a spectral distribution including red and blue spectral components; and filtering said spectral distribution of the received incident light to reduce the magnitude of blue spectral components relative to the magnitude of red spectral components to effect a change in the shape of the eye over time to treat the astigmatism in at least a portion of the field of view of an eye.

* * * * *